(12) United States Patent
Srinath et al.

(10) Patent No.: US 7,557,238 B2
(45) Date of Patent: Jul. 7, 2009

(54) PROCESS FOR THE PREPARATION OF TERT-BUTYL 6-CYANO-5-HYDROXY-3-OXOHEXANOATE

(75) Inventors: Sumithra Srinath, Karnataka (IN); Tom Thomas Puthiaparampil, Karnataka (IN); Sambasivam Ganesh, Karnataka (IN)

(73) Assignee: Biocon Limited (IN)

( * ) Notice: Subject to any disclaimer, the term of this patent is extended or adjusted under 35 U.S.C. 154(b) by 639 days.

(21) Appl. No.: 10/483,481

(22) PCT Filed: Sep. 18, 2003

(86) PCT No.: PCT/IN03/00317

§ 371 (c)(1), (2), (4) Date: Sep. 27, 2004

(87) PCT Pub. No.: WO2005/026107

PCT Pub. Date: Mar. 24, 2005

(65) Prior Publication Data

US 2005/0065362 A1    Mar. 24, 2005

(51) Int. Cl.
*C07C 255/03*    (2006.01)
(52) U.S. Cl. .................................................. 558/442
(58) Field of Classification Search .............. 558/442
See application file for complete search history.

(56) References Cited

U.S. PATENT DOCUMENTS

| | | | | |
|---|---|---|---|---|
| 5,155,251 A | * | 10/1992 | Butler et al. ............... | 558/442 |
| 5,216,174 A | * | 6/1993 | Butler et al. ............... | 548/517 |
| 6,274,740 B1 | | 8/2001 | Lin et al. | |
| 6,528,661 B2 | | 3/2003 | Niddam et al. | |
| 2002/0099224 A1 | | 7/2002 | Niddam et al. | |
| 2003/0114685 A1 | | 6/2003 | Niddam-Hildesheim et al. | |
| 2003/0175338 A1 | | 9/2003 | Singh et al. | |

FOREIGN PATENT DOCUMENTS

| | | |
|---|---|---|
| WO | WO 97/03960 | 2/1997 |
| WO | WO 02/43667 A2 | 6/2002 |
| WO | WO 03/004450 A1 | 1/2003 |
| WO | WO 03/004455 A2 | 1/2003 |
| WO | WO 03/004456 A1 | 1/2003 |
| WO | WO 03/016317 A1 | 2/2003 |

OTHER PUBLICATIONS

Oehrlein R et al., "Chemoenzymatic approach to statin side-chain building blocks" Advanced Synthesis Catalysis (2003), 345 (6+7), 713-715.
Woo et al., "Atorvastatin, an HMG-CoA reductase inhibitor and effective lipid-regulating agent. Part III. Syntheses of [2H5]-, [13C8], and [13C7, 15N] atorvastatin and their application in metabolic and pharmacokinetic studies", Journal of Labeled Compounds Radiopharmaceuticals (1999), 42(2), 135-145.
Lee et al., "Atorvastatin, an HMG-CoA reductase inhibitor and effective lipid-regulating agent. Part II. Synthesis of side chain-labled [14C] atorvastatin", Journal of Labeled Compounds Radiopharmaceuticals (1999), 42(2), 129-133.
Woo et al., "Atorvastatin, an HMG-CoA reductase inhibitor and effective lipid-regulating agent. Par I. Synthesis of ring-labeled [14C] atorvastatin", Journal of Labeled Compounds Radiopharmaceuticals (1999), 42(2), 121-127.
Radl et al., "An improved synthesis of 1,1-dimethylethyl-6-cyanomethyl-2,2-dimethyl-1,3-dioxane-4-acetate, a key intermediate for atorvastatin synthesis", Tetrahedron Letters (2002), 43(11), 2087-2090.
Manzoni et al., "Biosynthesis and biotechnological production of statins by filamentous fungi and application of these cholesterol-lowering drugs", Applied Microbiology and Biotechnology (2002), 58(5), 555-564.
Roth, Bruce D., "The discovery and development of atorvastatin, a potent novel hypolipidemic agent", Progress in Medicinal Chemistry (2002), 40, 1-22.
Wierzbicki, Anthony S., "Atorvastatin", Expert Opinion on Pharmacotherapy (2001), 2(5), 819-830.
Graul et al., "Atorvastatin calcium", Drugs of the future (1997), 22(9), 956-968.
Baumann et al., "The convergent synthesis of CI-981, an optically active, highly potent, tissue-selective inhibitor of HMG-CoA reductase", Tetrahedron Letters (1992), 33(17), 2283-2284.

* cited by examiner

*Primary Examiner*—James O. Wilson
*Assistant Examiner*—Ebenezer Sackey
(74) *Attorney, Agent, or Firm*—Choate, Hall & Stewart LLP

(57) ABSTRACT

In one aspect, the present invention provides a novel process for the preparation of tert-butyl 6-cyano-5-hydroxy-3-oxohexanoate, a key intermediate for the preparation of HMG-CoA reductase inhibitor.

3 Claims, No Drawings

PROCESS FOR THE PREPARATION OF TERT-BUTYL 6-CYANO-5-HYDROXY-3-OXOHEXANOATE

PRIORITY CLAIM

The present application claims the benefit under 35 U.S.C. § 371 of International Application No.: PCT/IN03/00317, filed Sep. 18, 2003, the entire contents of which is hereby incorporated herein by reference.

FIELD OF THE INVENTION

The present invention relates to a novel process for the preparation of tert-butyl 6-cyano-5-hydroxy-3-oxohexanoate, a key intermediate for the preparation of a HMG CoA reductase inhibitor.

BACKGROUND OF THE INVENTION

HMG CoA reductase inhibitors are pharmaceutically active compounds used for inhibition of cholesterol biosynthesis. A group of compounds called 'statins' comprising lovastatin, simvastatin, mevastatin, pravastatin, atorvastatin, rosuvastatin, cerivastatin and fluvastatin show antilipidemic activity and are widely known HMG CoA reductase inhibitors.

The ester derivative of the compound of Formula I

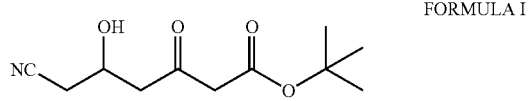

FORMULA I is a valuable chiral synthon for synthesizing atorvastatin.

SUMMARY OF THE INVENTION

In one aspect, the present invention provides a novel process for the preparation of the compound of Formula I. In another aspect, the process employs novel intermediates.

The present invention relates to a novel process for preparing a compound of Formula I

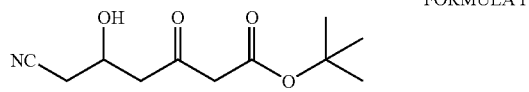

FORMULA I comprising
hydrolysis of a compound of Formula II

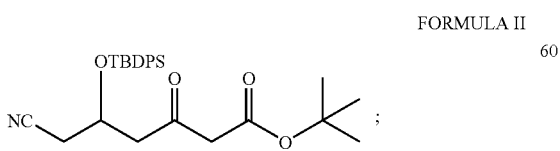

FORMULA II wherein, the compound of Formula II is obtained from a compound of Formula III

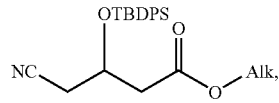

FORMULA III wherein Alk is a straight or branched $C_1$-$C_6$ alkyl; and
wherein the compound of Formula III is obtained from a compound of Formula IV

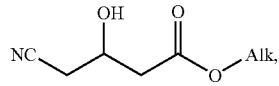

FORMULA IV wherein Alk is a straight or branched $C_1$-$C_6$ alkyl.

The process of the present invention has several advantages over the prior art including: higher yield during conversion of the compound of Formula III to the compound of Formula II as the hydroxy group is protected, reactions after protection with TBDPS can be followed by TLC, low consumption of reagents as the hydroxy group is protected, and reduced levels of undesired side products.

DETAILED DESCRIPTION OF CERTAIN PREFERRED EMBODIMENTS OF THE INVENTION

In one aspect, the present invention provides a novel process for the preparation of a compound of Formula I

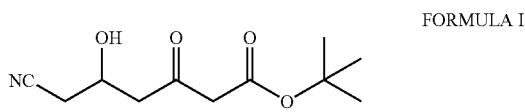

FORMULA I comprising
removal of the TBDPS group from a compound of Formula II

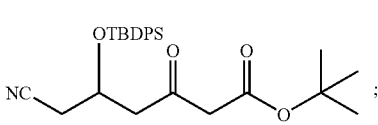

FORMULA II wherein the compound of Formula II is obtained from a compound of Formula III

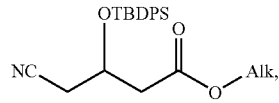

FORMULA III wherein Alk is a straight or branched $C_1$-$C_6$ alkyl; and
wherein the compound of Formula III is obtained from a compound of Formula IV

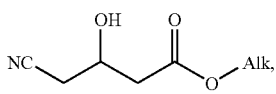

FORMULA IV wherein Alk is a straight or branched $C_1$-$C_6$ alkyl.

An exemplary process according to the present invention is depicted in Scheme I below:

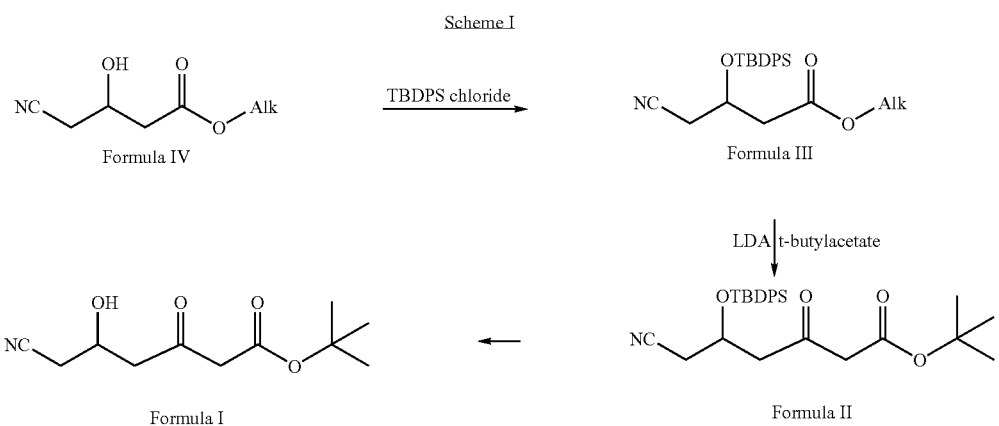

Scheme I wherein Alk is a straight or branched $C_1$-$C_6$ alkyl.

In one embodiment, the inventive process employs a hydroxy protecting group and utilizes novel intermediates of Formulae II and III. For example, TBDPS (tert-butyl diphenyl silyl) may be employed.

In certain exemplary embodiments, a compound of Formula I may be obtained by removal of the TBDPS group from a compound of Formula II by conventional methods.

In certain other embodiments, a compound of Formula II may be obtained by treating a compound of Formula III with a carbanion, which is generated by the reaction of tert-butyl acetate with lithium diisopropylamide.

In yet other embodiments, a compound of Formula III may be obtained by reacting a compound of Formula IV with tert-butyl diphenyl silyl chloride.

The illustrated embodiments have been set forth only for the purposes of example and should not be taken as limiting the invention. Therefore, it should be understood that, within the scope of the appended claims, the invention may be practiced other than specifically described herein.

Example 1

Ethyl 4-cyano-3-(tert-butyldiphenylsilyloxy)-butanoate

Imidazole (6.5 g, 0.095 mol) was added to a chilled solution (−5 to −10° C.) of ethyl 4-cyano-3-hydroxybutanoate (10 g, 0.063 mol) in dichloromethane (100 ml) under stirring, followed by tert-butyl diphenyl silyl chloride (15.7 g, 0.057 mol). After stirring for 4 hours at room temperature, water (250 ml) was added to the reaction mixture and layers separated. The aqueous layer was extracted with dichloromethane (100 ml) and combined with the organic layer. The combined organic layer was evaporated to give title compound.

Yield: 22 g.

Example 2 tert-Butyl 6-cyano-5-(tert-butyldiphenylsilyloxy)-3-oxohexanoate

A solution of n-butyl lithium in hexane (14.4 ml, 0.21 mol) was added to a chilled solution (−5 to −10° C.) of diisopropylamlie (23.2 g, 0.23 mol) in THF (100 ml) and the resulting mixture was stirred at −5 to −10° C. for 30 minutes. After chilling the reaction to about −45° C., tert-butyl acetate (26 g, 0.21 mol) was added and the resulting reaction mixture was stirred at −20-30° C. for 1 hour. A solution of ethyl 4-cyano-3-(tert-butyldiphenylsilyloxy)-butanoate (20 g, 0.050 mol) in THF (20 ml) was added to the reaction mixture at about −75° C. and further stirred −70-−75° C. for 2 hours. Methanol (15 ml) was added to the reaction mixture followed by water (200 ml) and layers were separated. The organic layer was preserved. The aqueous layer was extracted with ethyl acetate (2×200 ml) and combined with the organic layer. The combined organic layer was evaporated to give the title compound.

Yield: 20 g.

We claim:

1. A process for the preparation of a compound of Formula I:

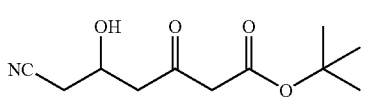

FORMULA I comprising removing the tert-butyl diphenyl silyl group of a compound of Formula II:

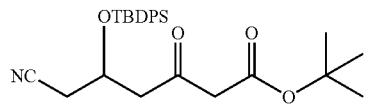

FORMULA II wherein the compound of Formula II is obtained by treating a compound of Formula III:

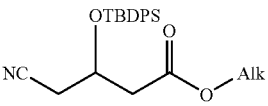

FORMULA III wherein Alk is a straight or branched $C_1$-$C_6$ alkyl, with a carbanion generated by the reaction of tert-butyl acetate with lithium diisopropylamide, and
wherein the compound of Formula III is obtained from reacting a compound of Formula IV:

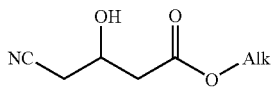

FORMULA IV wherein Alk is a straight or branched $C_1$-$C_6$ alkyl, with tert-butyl diphenyl silyl chloride.

2. A compound of Formula II:

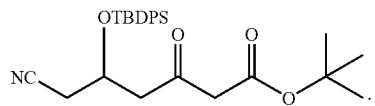

FORMULA II

3. A compound of Formula III:

FORMULA III wherein Alk is a straight or branched $C_1$-$C_6$ alkyl.

* * * * *